United States Patent [19]
Mager et al.

[11] Patent Number: 5,609,651
[45] Date of Patent: Mar. 11, 1997

[54] OXIDATION HAIR DYE COMPOSITION MADE FROM A CREAMY HAIR DYE-CONTAINING CARRIER AND A PREPARATION CONTAINING AN OXIDIZING AGENT AND POLYMER AND METHOD FOR OXIDATIVE DYEING OF HAIR

[75] Inventors: Herbert Mager; Johann Aeby, both of Marly, Switzerland

[73] Assignee: Wella Aktiengesellschaft, Darmstadt, Germany

[21] Appl. No.: 547,374

[22] Filed: Oct. 24, 1995

Related U.S. Application Data

[63] Continuation of Ser. No. 301,299, Sep. 6, 1994, abandoned.

[30] Foreign Application Priority Data

Sep. 28, 1993 [DE] Germany ............ 43 32 965.9

[51] Int. Cl.$^6$ ........................................... A61K 7/13
[52] U.S. Cl. ............... 8/435; 8/406; 8/407; 8/408; 8/552; 8/907
[58] Field of Search ............... 8/405, 406, 407, 8/408, 435, 552, 609, 907

[56] References Cited

U.S. PATENT DOCUMENTS

| | | | |
|---|---|---|---|
| 3,912,808 | 10/1975 | Sokol | 8/406 |
| 4,517,174 | 5/1985 | Jacquet et al. | 8/405 |
| 4,927,627 | 5/1990 | Schrader et al. | 8/406 |
| 4,970,066 | 11/1990 | Grollier et al. | 8/406 |
| 5,102,655 | 4/1992 | Yoshihara et al. | 8/405 |

FOREIGN PATENT DOCUMENTS

| | | |
|---|---|---|
| 4005008 | 8/1991 | Germany. |
| 53-078985 | 7/1978 | Japan. |
| 55-049308 | 4/1980 | Japan. |
| 55049308 | 9/1990 | Japan. |

OTHER PUBLICATIONS

English language translation of Nippon Oils & Fats KK, JP 55–49308, Apr. 9, 1980, pp. 1–11.

"Cosmetics, Science and Technology", E. Sagarin, 1957, pp. 503–511.

CFTA International Cosmetic Ingredient Dictionary, vol. 4, 1991, pp. 475–490.

Handbuch der Kosmetika und Riechstoffe, vol. 3, H. Janistyn, 1973, pp. 388–397.

Technology of Colour Change, Top Hair, No. 21, pp. 92 to 98, Nov. 1992.

*Primary Examiner*—Paul Lieberman
*Assistant Examiner*—Caroline L. Dusheck
*Attorney, Agent, or Firm*—Michael J. Striker

[57] ABSTRACT

The oxidation hair dye composition is made by mixing a viscous creamy hair dye-containing carrier and a fluid preparation in a weight ratio of dye-containing carrier to fluid preparation of 2:1 to 1:3. The viscous creamy hair dye-containing carrier has a viscosity of at least 10,000 mPa.s and contains 0.01 to 12 percent by weight of a combination of developer substance and coupler substance and 15 to 60 percent by weight of a thickener mixture containing fatty alcohols having from 10 to 24 carbon atoms, fatty acid esters, petrolatum, thickened polyacrylic acid derivatives, nonylphenol ethoxylated with 2 to 8 moles of ethylene oxide, fatty acids, starch and/or spermaceti. The fluid preparation contains 0.1 to 20 percent by weight of an oxidizing agent and 0.01 to 6 percent by weight of a nonionic polymer of formula (I), $$R-(O-CH(CH_3)-CH_2)_x-(O-CH_2-CH_2)_y-OH \qquad (I)$$

wherein R is an alkyl group having from 1 to 25 carbon atoms, a hydroxyalkyl group having from 2 to 25 carbon atoms or a dihydroxyalkyl groups having from 3 to 25 carbon atoms, and x=a whole number from 10 to 200, y=a whole number from 0 to 200 and x+y≧20. A method for oxidative dyeing of hair is also described using this oxidative hair dyeing composition.

12 Claims, No Drawings

OXIDATION HAIR DYE COMPOSITION MADE FROM A CREAMY HAIR DYE-CONTAINING CARRIER AND A PREPARATION CONTAINING AN OXIDIZING AGENT AND POLYMER AND METHOD FOR OXIDATIVE DYEING OF HAIR

This application is a continuation of application Ser. No. 08/301,299, filed Sep. 6 1994, now abandoned.

BACKGROUND OF THE INVENTION

The present invention relates to an oxidation hair dye composition made by mixing a creamy hair dye-containing carrier and a preparation containing an oxidizing agent and polymer and also to a method of oxidative dyeing of hair with that hair dye composition.

Oxidation hair dye compositions have attained substantial significance in the hair dyeing arts. The hair dyeing occurs in the hair shaft by a reaction between a developer substance with a coupler substance in the presence of a suitable oxidizing agent.

Particularly 2,5-diaminotoluene, 4-aminophenol, 4-amino-3-methylphenol, 1,4-diaminobenzene, 2-(2'-hydroxyethyl)-1,4-diaminobenzene, 2,5-diaminobenzyl alcohol and tetraaminopyrimidine are used as developer substances. Coupler substances advantageously used include 1-naphthol, resorcinol, 4-chlororesorcinol, sesamol, m-aminophenol, 5-amino-o-cresol, 2-amino-4-(2'-hydroxyethyl)amino anisole, 2,4-diaminoanisole and 2,4-diaminophenetole.

A broad palette of different color shades can be produced by suitable combinations of developer and coupler substances.

Oxidation hair dye compositions are made from two components, which are quickly mixed prior to use. Then the mixture is applied to the hair. The first component, the hair dye-containing carrier, contains the effective hair dyeing substances and can be in the form of a solution, a gel or a cream. The second component is a product in which a suitable oxidizing agent, for example hydrogen peroxide, is contained.

The hair dye-containing carrier in the form of a high viscosity cream is mixed with a fluid or emulsion-forming aqueous hydrogen peroxide solution and the resulting preparation is applied with a brush to the hair. The use of the thick liquid hair dye containing cream is then particular advantageous, when hair which is very gray is to be dyed. A complete and uniform covering of the gray is then obtained, since a high viscosity cream can be applied to the hair in a thicker layer and with a brush than a low viscosity preparation, which tends to run off the hair.

This type of high viscosity hair dye containing cream has several disadvantages as well as the above-described advantages. The high viscosity hair dye-containing mass can be mixed only with some difficult with the fluid hydrogen peroxide solution to form a single hair dyeing composition. Furthermore application using an application bottle or flask is not possible because of the high viscosity and poor flow properties.

Because of these considerations in practice high viscosity dye-containing creams and special low viscosity preparations suitable for use in application bottles or flasks are used side-by-side.

It is then necessary to develop a variety of different formulations, which are suitable either for application with a brush or for application with a application bottle.

This is not only connected with a higher development cost but also leads to superfluous product and raw material varieties, whereby, among other things, higher storage costs arise in both manufacturing and also in marketing.

SUMMARY OF THE INVENTION

It is an object of the present invention to provide an appropriate modification of the standard creamy hair dye-containing carrier applied with a brush to allow the use of this creamy hair-dye containing carrier in application bottles.

It has now been surprisingly found that a standard high viscosity cream-like hair dye-containing carrier or mass can be applied by means of an application flask or bottle when an oxidizing agent-containing preparation containing a nonionic polymer is used with it.

The oxidation hair dye composition according to the invention is made by mixing (A) a high viscosity or viscous creamy hair dye-containing carrier and (B) a fluid or emulsion-form preparation containing an oxidizing agent and a nonionic polymer of formula I

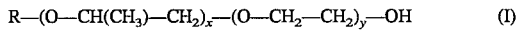

$$R\text{—}(O\text{—}CH(CH_3)\text{—}CH_2)_x\text{—}(O\text{—}CH_2\text{—}CH_2)_y\text{—}OH \qquad (I)$$

wherein R is an alkyl group with from one to 25 carbon atoms, a hydroxyalkyl group with from 2 to 25 carbon atoms or a dihydroxyalkyl group with from 3 to 25 carbon atoms; and x=a whole number from 0 to 200;
y=a whole number from 0 to 200; and
x+y≧20.

The oxidation hair dye according to the invention permits outstanding hair dyeing and good coverage of gray hair and is exceptionally well suited for application from a bottle or flask because of its comparatively low viscosity, its outstanding flow properties and the good miscibility of components (A) and (B).

The weight ratio of the hair dye-containing carrier or mass (A) to the preparation (B) varies from 2:1 to 1:3. A weight ratio of 1:1 is particularly preferred.

The viscosity of the marketed high dyeing composition according to the invention for oxidative dyeing of hair is advantageously from 500 to 3000 mPa.s. The viscosity of the component (A) amounts advantageously to at least 10,000 mPa.s, while that of component (B) advantageously has a maximum of 2000 mPa.s.

For example, the compounds described on pages 475 to 490 in CTFA-International Cosmetic Ingredient Dictionary, Volume 4(1991) are suitable as nonionic polymers of formula I. These compounds include polyoxyethylene(10)polyoxypropylene(7)butyl ether, polyoxyethylene(30)polyoxypropylene(20)butyl ether, polyoxyethylene(20)polyoxypropylene(10)cetyl/stearyl ether, polyoxyethylene(20)polyoxypropylene(5)cetyl ether, polyoxyethylene(10)polyoxypropylene(20)decyltetradecyl ether, polyoxyethylene(24)polyoxypropylene(24)glyceryl ether, polyoxyethylene(50)polyoxypropylene(12)lanoline ether, polyoxyethylene(12)polyoxypropylene(66)glyceryl ether, and, particularly preferred, polyoxyethylene(45)polyoxypropylene(33)butyl ether and polyoxyethylene(37)polyoxypropylene(38)butyl ether.

The nonionic polymer of formula (I) is used in an amount of from 0.01 to 6 percent by weight in the preparation (B).

The preparation (B) contains beside this polymer of formula (I) 0.1 to 20 percent by weight, advantageously 2 to 14 percent by weight of an oxidizing agent. Hydrogen peroxide, and its addition compounds with urea, melamin and sodium borate are preferred as oxidizing agents. Hydrogen peroxide is especially preferred as oxidizing agent.

The preparation (B) can also contain conventional materials, for example thickeners, particularly fatty alcohols, fatty acid esters and petrolatum; emulsifiers, especially sodium lauryl alcohol diglycol ether sulfate, and cholesterol; perfume oils, stabilizers, especially salicylic acid and p-hydroxybenzoic acid ester; inorganic acids, especially phosphoric acid; and complex formers and turbidity producing agents.

The high viscosity or viscous hair dye-containing carrier (A) contains 15 to 60 percent by weight of a thickener mixture, which advantageously comprises at least 50 percent by weight of a fatty alcohol having from 10 to 24 carbon atoms, advantageously cetyl alcohol and stearyl alcohol or their mixture. Besides these fatty alcohols the thickened mixture can also contain commercial thickeners, for example fatty acid esters; petrolatum; fatty alcohols ethoxylated with 2 to 6 moles ethylene oxide; nonylphenol ethoxylated with 2 to 8 moles of ethylene oxide; fatty acids, e.g. oleic acid, starch; spermaceti or thickening polyacrylic acid derivatives.

Furthermore the hair dye-containing carrier or mass (A) can also contain nonionic, anionic or amphoteric emulsifiers, e.g. sodium lauryl ether sulfate, sodium lauryl sulfate, ammonium lauryl sulfate, potassium stearate, cetyl alcohol polyethylene glycol ether, ethoxylated castor oil, cocoa fatty acid amido propyl betaine and cocoalkyldimethyl ammonium betaine; cholesterol; wool wax alcohol; antioxidants, e.g. ascorbic acid or sodium sulfite; complex formers; perfume oils, solvents, e.g. ethanol, isopropanol, 1,3-butanediol, propyleneglycol and glycerin; or cationic polymers.

The above-named additives are contained in the hair dye-containing mass (A) in the usual amounts for this type of composition, e.g. the solvents are contained in amounts from 1 to 10 percent, the perfume oils in an amount of from 0.01 to 1 percent by weight, the cationic polymers in an amount of from 0.05 to 1 percent by weight and the antioxidants and complex formers in an amount of 0.01 to 0.5 percent by weight.

The hair dye-containing mass (A) has a pH value of 3.5 to 12.5. The pH value is advantageously adjusted with ammonia. An organic amine, e.g. monoethanolamine or an inorganic alkali such as caustic soda solution.

The hair dye-containing carrier (A) contains at least one coupler substance and at least one developer substance as well as additional self-coupling and direct dyes to be applied to the hair as needed. The developer and coupler substances are used in the hair dyeing composition either as such or in the form of physiologically acceptable salts, e.g. the chloride, sulfate, phosphate, acetate, propionate, lactate or citrate salts.

The coupler substance is used generally in approximately equimolar amounts with the developer substance. Although equimolar amounts of coupler and developer substance have proven useful, it is however not disadvantageous when the coupler substance is in a certain excess or deficit in relation to the developer substance. It is also not necessary that the developer and coupler components be present in a single product. Furthermore the developer component can be a mixture of known developer substances and the coupler component can be a mixture of known coupler substances.

The hair dye-containing carrier or mass (A) contains the following known coupler substances, alone or together with each other in a mixture, particularly 1-naphthol, 4-methoxy-1-naphthol, resorcinol, 4-chlororesorcinol, 4,6-dichlororesorcinol, 2-methylresorcinol, 3-aminophenol, 3-amino-6-methylphenol, 4-hydroxy- 1,2-methylenedioxybenzene, 4-amino-1,2-methylenedioxybenzene, 4-(2'-hydroxyethylamino)-1,2-methylenedioxybenzene, 4-hydroxyindole, 2,3-dimaino-6-methoxypyridine and 5-amino-2-methylphenol. Furthermore additional suitable coupler substances include 2,4-dihydroxyphenol ethers like 2,4-dihydroxyanisole and 2,4-dihydroxyphenoxyethanol.

The developer substance component of the hair dye-containing carrier, above all, is selected from the group consisting of the following known developer substances: 1,4-diaminobenzene, 2,5-diaminotoluene, 2,5-diaminobenzylalcohol, 3-methyl-4-aminophenol, 2-(2'-hydroxyethyl)-1,4-diaminobenzene, tetraaminopyrimidine and 4-aminophenol.

The known hair dyes and standard oxidation hair dyes, which can be contained in the hair dye-containing mass (A) of the invention are, among others, described in the reference book by E. Sagarin "Cosmetics, Science and Technology", Interscience Publishers Inc., New York (1957), pp. 503 ff and the book by H. Janistyn, "Handbuch der Kosmetika under Riechstoffe", (1973), pp. 388 ff. The total amount of the developer-coupler substance combination contained in the hair dye-containing mass (A) amounts to 0.01 to 12 percent by weight, particularly 0.2 to 4 percent by weight.

To obtain particular color shades or nuances also direct dyes, especially triphenylmethane dyes such as Basic Violet 14 (C.I. 42 510) and Basic Violet 2 (C.I. 42 520), aromatic nitrodyes such as 2-amino-4,6-dinitrophenol, 2-nitro-4-(2'-hydroxyethylamino)-aniline and 2-amino-4-nitrophenol, azodyes such as Acid Brown 4 (C.I. 14 805) and Acid Blue 135 (C.I. 13 385), Anthraquinone dyes such as Disperse Violet 4 (C.I. 61 105), Disperse Blue (C.I. 64 500), Disperse Red 15 (C.I. 60 710), Disperse Violet 1 (C.I. 61 100), also 1,4,5,8-tetraaminoanthraquinone and 1,4-diaminoanthraquinone, are for example contained in the hair dye-containing mass (A).

The hair dye-containing mass (A) can also contain self-coupling dye precursors, such as 2-amino-5-methylphenol, 2-amino-6-methylphenol, 2-amino-5-ethoxyphenol or also 2-propylamino-5-aminopyridine.

The total amount of the direct dye compounds and the self-coupling dye precursors contained in the hair dye-containing mass (A) amounts to 0.01 to 6 percent by weight, advantageously 0.2 to 4 percent by weight.

The total amount of all hair dye compounds, thus the developer-coupler substance combination, the self-coupling dye precursors and the direct hair dyes, in the hair dye-containing carrier (A) amounts to 0.1 to 14 percent by weight, advantageously 0.2 to 8 percent by weight.

The ready-for-use oxidation hair dye composition obtained by mixing the hair dye-containing carrier (A) with the preparation (B) containing the oxidizing agent for oxidative dyeing of hair can be an acidic, neutral or alkaline composition. The pH-value of the composition according to the invention for oxidative dyeing of hair is advantageously between 7.5 to 12, particularly from 9.5 to 10.5.

The above-mentioned weight percentages are thus based on the total amount of hair dye-containing carrier (A) or, as the case may be, to the total amount of the preparation (B) if nothing else is stated to the contrary.

The method of dyeing hair according to the invention comprises the steps of (a) prior to use, mixing the creamy hair dye-containing carrier (A) directly with the preparation (B) containing the oxidizing agent in weight ratios of 2:1 to 1:3, advantageously 1:1, to make the oxidation hair dye composition, (b) applying to the hair an amount of a hair dye composition made in step (a) which is sufficient to dye hair, according to the amount of hair being dyed from 90 to 160 grams, with the help of an application bottle or flask, (c) allowing the hair dye composition to act on the hair for about 10 to 45 minutes, advantageously 30 minutes, at about 15° to 50° C., and (d) rinsing the hair with water after the hair dye composition acts on the hair in step c) and then drying it. If necessary prior to drying the hair is washed and/or after-rinsed with a solution of a physiologically acceptable organic acid, e.g. citric acid or tartaric acid.

The subsequent examples clearly illustrate the subject matter of the invention.

EXAMPLES

Example 1: Oxidation Hair Dye Composition

Creamy hair dye-containing carrier (A1)

| | |
|---|---|
| 25.000 g | cetyl stearyl alcohol |
| 0.600 g | wool wax alcohol |
| 0.200 g | cholesterol |
| 6.800 g | sodium lauryl alcohol diglycol ether sulfate, 28 percent by weight aqueous solution, |
| 0.500 g | sodium sulfite, water free |
| 1.350 g | 2,5-diaminotoluene sulfate |
| 0.720 g | resorcinol |
| 0.056 g | m-aminophenol |
| 0.028 g | m-phenylenediamine |
| 7.282 g | ammonia, 25-percent by weight aqueous solution, |
| 57.464 g | water |
| 100. | |

Hydrogen peroxide Preparation (B1)

| | |
|---|---|
| 12.0 g | Hydrogen peroxide, 50-percent by weight aqueous solution |
| 2.0 g | Polyoxyethylene(45)polyoxypropylene(33)butyl ether (Unilube ® MB50-168R of the Nippon Oil & Fats Co., Ltd.; Tokyo/JAPAN) |
| 1.0 g | Cetyl stearyl alcohol |
| 0.2 g | Sodium lauryl sulfate |
| 0.1 g | Polyethyleneglycol(25)cetyl/stearyl ether (Cremophor ® A25 of BASF AG; Ludwigshaften/DE) |
| 84.7 g | Water |
| 100. | |

The pH value of the hydrogen peroxide preparation (B1) is adjusted with dilute phosphoric acid to 2.5.

50 grams of the hair dye-containing carrier (A1) and 50 grams of the hydrogen peroxide preparation (B1) are mixed in a 200 ml application bottle or flask by shaking or agitation. The shaking process can occur without difficulty and results after a brief shaking period in a completely homogeneous mixture, which can be applied to the hair without problem from the application bottle or flask.

The hair dyeing composition so obtained is applied to completely gray hair. After an acting time of 30 minutes at room temperature the hair dyeing composition is rinsed from the hair. Subsequently the hair is washed with a shampoo, rinsed with water and then dried. The hair so treated is dyed from the hair roots to the hair tips a uniform dark brown.

Example 2: Oxidation Hair Dye Composition

Creamy hair dye-containing carrier (A2)

| | |
|---|---|
| 21.000 g | Cetyl stearyl alcohol |
| 4.750 g | glycerin monodistrearate, self emulsifying |
| 4.000 g | Sodium lauryl alcohol diglycol ether sulfate, 28 percent by weight aqueous solution, |
| 2.000 g | Polyethyleneqlvcol(25)cetyl/stearyl ether (Cremophor ® A25 of BASF AG; Ludwigshaften/DE) |
| 0.700 g | Cholesterol |
| 0.300 g | Resorcinol |
| 0.300 g | m-phenylenediamine |
| 0.200 g | ascorbic acid |
| 5.00 g | ammonia, 35-percent aqueous solution |
| 61.75 g | water |
| 100. | |

Hydrogen peroxide Preparation (B2)

| | |
|---|---|
| 12.0 g | Hydrogen peroxide, 50-percent by weight aqueous solution |
| 4.0 g | Polyoxyethylene(45)polyoxypropylene(33)butyl ether (Unilube ® MB50-168R of the Nippon Oil & Fats Co., Ltd.; Tokyo/JAPAN) |
| 84.0 g | Water |
| 100. | |

The pH value of the hydrogen peroxide preparation (B2) is adjusted with dilute phosphoric acid to 2.5.

50 grams of the hair dye-containing carrier (A2) and 50 grams of the hydrogen peroxide preparation (B2) are mixed in an application bottle or flask by shaking or agitation. The shaking process can occur without difficulty and results after a brief shaking period in a completely homogeneous mixture, which can be taken out nearly completely from the application bottle or flask.

The hair dyeing composition so obtained is applied to completely gray hair. After an acting time of 30 minutes at room temperature the hair dyeing composition is rinsed from the hair. Subsequently the hair is washed with a shampoo, rinsed with water and then dried. The hair so treated is dyed from the hair roots to the hair tips a uniform dark blond.

Example 3. Comparative Experiments

Experiment I

An oxidation hair dye composition according to Example 1 comprising components (A1) and (B1) is compared with a mixture of components (A1) and (C). The hair dye coloring properties of these two mixtures, their viscosity, the miscibility of both components of the mixtures and their application by means of an application bottle or flask were compared. The component (C) differs from the component (B1) because the polyoxyethylene(45)polyoxypropylene(33) butyl ether in it is replaced by an equal amount of water.

The application of the mixture and the oxidation hair dye composition according to the invention occurs as described in Example 1.

The results of these comparative experiments are assembled in the following Table I.

TABLE I

Comparison of Properties of an Oxidation Hair Dye Composition of the Invention with a Composition which is not of the Invention.

| | Hair Dye Composition of the Invention (A1) + (B1) | Hair Dye Composition not of the Invention (A1) + (C) |
|---|---|---|
| Color of Dyed Hair | The same in both cases | |
| Mixability of both components | Very Good; Homogeneous after 10 seconds | Mixable only with difficulty with agitation with comparatively large energy consumption |
| Viscosity | medium to low viscosity | High viscosity |
| Application by bottle | problem-free application, almost 15 to 18% remains in the application flask | difficult to apply, more than 30% remains in the bottle |

Experiment II

An oxidation hair dye composition according to example 2 comprising the components (A2) and (B2) is compared to a mixture of component (A2) and (D2). The components (D) differs from the component (B2) only in that the polyoxyethylene(45)polyoxypropylene(33) butyl ether in it is replaced by an equal amount of water.

The application of both the mixture and the oxidation hair dye composition according to the invention to the hair occurs as described in Example 2.

The results are summarized in Table II below.

TABLE II

Comparison of Properties of an Oxidation Hair Dye Composition of the Invention with a Composition which is not of the Invention.

| | Hair Dye Composition of the Invention (A1) + (B1) | Hair Dye Composition not of the Invention (A1) +(D) |
|---|---|---|
| Dyed Hair | The same in both cases | |
| Mixability of both components | Very Good; Homogeneous after less than 10 seconds | Mixable only with difficulty with agitation |
| Viscosity | medium to low viscosity | High viscosity |
| Application by bottle | problem-free application, at most 15% remains in the application flask | difficult to apply more than 30% remains in the bottle |

If nothing is stated to the contrary all percentages in the present application are percentages by weight.

Measurements of viscosity were performed with a Viscobalance of the Haake Firm, Type VW, Bar 2; weight applied: 20 grams; and measurement temperature 20° C.

While the invention has been illustrated and described as embodied in an oxidation hair dye composition made by mixing a creamy hair dye-containing carrier and a preparation containing an oxidizing agent and polymer and also in a method of oxidative dyeing of hair with that hair dye composition, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. An oxidation hair dye composition made by mixing a viscous creamy hair dye-containing carrier and a fluid preparation, wherein said viscous creamy hair dye-containing carrier has a viscosity of at least 10,000 mPa.s and contains 0.01 to 12 percent by weight of a combination of at least one developer substance and at least one coupler substance and 15 to 60 percent by weight of a thickener mixture containing at least one member selected from the group consisting of fatty alcohols having from 10 to 24 carbon atoms, fatty acid esters, petrolatum, thickened polyacrylic acid derivatives, nonylphenol ethoxylated with 2 to 8 moles of ethylene oxide, fatty acids, starch and spermaceti; and wherein said fluid preparation contains 0.1 to 20 percent by weight of an oxidizing agent and 0.01 to 6 percent by weight of a nonionic polymer of formula (I), $$R-(O-CH(CH_3)-CH_2)_x-(O-CH_2-CH_2)_y-OH \qquad (I)$$

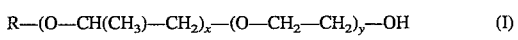

wherein R is selected from the group consisting of alkyl groups having from 1 to 25 carbon atoms, hydroxyalkyl groups having from 2 to 25 carbon atoms and dihydroxyalkyl groups having from 3 to 25 carbon atoms, and x=a whole number from 10 to 200;

y=a whole number from 0 to 200; and x+y≧20, and a weight ratio of said creamy hair dye-containing carrier to said fluid preparation in said mixing is from 2:1 to 1:3.

2. An oxidation hair dye composition as defined in claim 1, wherein said nonionic polymer is selected from the group consisting of polyoxyethylene(45)polyoxypropylene(33) butyl ether, polyoxyethylene(37)polyoxypropylene(38)butyl ether polyoxyethylene(30)polyoxypropylene(20)butyl ether, polyoxyethylene(20)polyoxypropylene(10)cetyl/stearyl ether, polyoxyethylene(10)polyoxypropylene(20)decyltetradecyl ether, polyoxyethylene(24)polyoxypropylene(24) glyceryl ether, polyoxyethylene(50)polyoxypropylene(12) lanoline ether and polyoxyethylene(12)polyoxypropylene (66)glyceryl ether.

3. An oxidation hair dye composition as defined in claim 1, wherein said thickener mixture comprises at least 50 percent by weight of a fatty alcohol having 10 to 24 carbon atoms.

4. An oxidation hair dye composition as defined in claim 1, wherein said creamy hair dye-containing carrier contains 0.01 to 6 percent by weight of direct-dyeing hair dyes and self-coupling hair dye precursors.

5. An oxidation hair dye composition as defined in claim 1, wherein said creamy hair dye-containing carrier contains 0.1 to 14 percent by weight of a total amount of dye components, said dye components consisting of a combination of at least one developer substance and at least one coupler substance, direct-dyeing hair dyes and self-coupling hair dye precursors.

6. An oxidation hair dye composition as defined in claim 1, wherein said oxidizing agent is hydrogen peroxide.

7. An oxidation hair dye composition as defined in claim 1, wherein said fluid preparation is an emulsion.

8. Method of dyeing hair comprising the steps of:
a) mixing a creamy hair dye-containing carrier prior to use with a fluid preparation containing an oxidizing agent in weight ratios of 2:1 to 1:3 to make an oxidation hair dye composition, wherein said creamy hair dye-containing carrier has a viscosity of at least 10,000 mPa.s and contains 0.01 to 12 percent by weight of a combination of at least one developer substance and at least one coupler substance and 15 to 60 percent by weight of a thickener mixture containing at least one member selected from the group consisting of fatty alcohols having from 10 to 24 carbon atoms, fatty acid esters, petrolatum, thickened polyacrylic acid derivatives, nonylphenol ethoxylated with 2 to 8 moles of ethylene oxide, fatty acids, starch and spermaceti; and said fluid preparation contains 0.1 to 20 percent by weight of an oxidizing agent and 0.01 to 6 percent by weight of a nonionic polymer of formula (I),

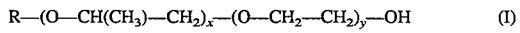

R—(O—CH(CH$_3$)—CH$_2$)$_x$—(O—CH$_2$—CH$_2$)$_y$—OH   (I)

and R is selected from the group consisting of alkyl groups having from 1 to 25 carbon atoms, hydroxyalkyl groups having from 2 to 25 carbon atoms and dihydroxyalkyl groups having from 3 to 25 carbon atoms, and x=a whole number from 10 to 200;
y=a whole number from 0 to 200; and
x+y≧20;

b) applying to hair an amount of a hair dye composition made in step (a) by means of an application bottle, said amount of said hair dye composition being sufficient to dye said hair and being from 90 to 160 grams, depending on the amount of hair to be dyed;

c) allowing the hair dye composition to act on the hair for about 10 to 45 minutes at about 15° to 50° C.; and d) rinsing the hair with water after the hair dye composition acts on the hair in step c) and then drying the hair.

9. Method as defined in claim 8, wherein said preparation contains 0.01 to 6 percent by weight of said nonionic polymer and 0.1 to 20 percent by weight of said oxidizing agent and said creamy hair-dye containing carrier contains 0.01 to 12 percent by weight of a combination of at least one developer substance and at least one coupler substance and said thickener mixture contains at least 50 percent by weight of one of said fatty alcohols having from 10 to 24 carbon atoms.

10. Method as defined in claim 9, wherein said fluid preparation is an emulsion and said oxidizing agent is hydrogen peroxide.

11. An oxidation hair dye composition made by mixing a viscous creamy hair dye-containing carrier and a fluid preparation so that the composition has a viscosity between 500 mPa.s and 3000 mPa.s, wherein a weight ratio of said creamy hair dye-containing carrier to said fluid preparation in the mixing is from 2:1 to 1:3, said creamy hair-dye containing carrier has a viscosity of at least 10,000 mPa.s and contains 0.01 to 12 percent by weight of a combination of at least one developer substance and at least one coupler substance and 15 to 60 percent by weight of a thickener mixture containing at least one member selected from the group consisting of fatty alcohols having from 10 to 24 carbon atoms, fatty acid esters, petrolatum, thickened polyacrylic acid derivatives, nonylphenol ethoxylated with 2 to 8 moles of ethylene oxide, fatty acids, starch and spermaceti, and said fluid preparation has a viscosity of at most 2000 mPa.s and contains 0.1 to 20 percent by weight of an oxidizing agent and 0.01 to 6 percent by weight of a nonionic polymer, wherein said nonionic polymer is selected from the group consisting of polyoxyethylene(45)polyoxypropylene(33)butyl ether, polyoxyethylene(37)polyoxypropylene(38)butyl ether, polyoxyethylene(30)polyoxypropylene(20)butyl ether, polyoxyethylene(20)polyoxypropylene(10)cetyl/stearyl ether, polyoxyethylene(10)polyoxypropylene(20)decyltetradecyl ether, polyoxyethylene(24)polyoxypropylene(24)glyceryl ether, polyoxyethylene(50)polyoxypropylene(12)lanoline ether and polyoxyethylene(12)polyoxypropylene(66)glyceryl ether.

12. An oxidation hair dye composition as defined in claim 11, wherein said nonionic polymer is polyoxyethylene(45)polyoxypropylene(33)butyl ether.

* * * * *